US008864705B2

(12) United States Patent
Nishigishi (10) Patent No.: US 8,864,705 B2
(45) Date of Patent: Oct. 21, 2014

(54) BALLOON CATHETER

(75) Inventor: Makoto Nishigishi, Seto (JP)

(73) Assignee: Asahi Intecc Co., Ltd., Nagoya-shi (JP)

( * ) Notice: Subject to any disclaimer, the term of this patent is extended or adjusted under 35 U.S.C. 154(b) by 28 days.

(21) Appl. No.: 13/407,340

(22) Filed: Feb. 28, 2012

(65) Prior Publication Data

US 2012/0226231 A1  Sep. 6, 2012

(30) Foreign Application Priority Data

Mar. 4, 2011 (JP) .................................. 2011-047083

(51) Int. Cl.
*A61M 31/00* (2006.01)
*A61M 37/00* (2006.01)
*A61M 25/01* (2006.01)
*A61M 25/00* (2006.01)
*A61M 25/10* (2013.01)

(52) U.S. Cl.
CPC ..... *A61M 25/104* (2013.01); *A61M 2025/0183* (2013.01); *A61M 2025/0063* (2013.01); *A61M 25/0102* (2013.01); *A61M 25/1006* (2013.01)
USPC .............. 604/103.09; 604/103.1; 604/103.11; 604/103.12

(58) Field of Classification Search
USPC ............... 604/103.09, 103.1, 103.11, 103.12, 604/96.01, 164.01
See application file for complete search history.

(56) References Cited

U.S. PATENT DOCUMENTS

| 5,607,394 | A | 3/1997 | Andersen et al. |
| 5,810,867 | A | 9/1998 | Zarbatany et al. |
| 5,823,995 | A | 10/1998 | Fitzmaurice et al. |
| 6,475,187 | B1 | 11/2002 | Gerberding |
| 6,589,207 | B1 | 7/2003 | El-Nounou |
| 6,733,473 | B1 * | 5/2004 | Reifart et al. .............. 604/96.01 |
| 8,088,121 | B2 | 1/2012 | Nishide et al. |
| 2005/0049552 | A1 * | 3/2005 | Holzapfel et al. ....... 604/103.04 |
| 2009/0270801 | A1 | 10/2009 | Shimada et al. |

FOREIGN PATENT DOCUMENTS

| CN | 101001659 A | 7/2007 |
| EP | 1163925 A1 | 12/2001 |
| EP | 1787673 A1 | 5/2007 |
| EP | 1 880 742 A1 | 1/2008 |
| JP | A-08-500505 | 1/1996 |
| JP | A-09-503411 | 4/1997 |
| JP | A-2002-505166 | 2/2002 |
| JP | A-2002-291899 | 10/2002 |
| JP | A-2003-517901 | 6/2003 |
| WO | WO 00/33910 A1 | 6/2000 |
| WO | WO 2006/109649 A1 | 10/2006 |

OTHER PUBLICATIONS

Jul. 12, 2012 Search Report issued in European Patent Application No. 12152565.3.
Notification of Reasons for Refusal issued in Japanese Patent Application No. 2011-047083 dated Feb. 20, 2014 (w/ translation).
Aug. 5, 2014 Office Action issued in Chinese Patent Application No. 201210001871.6 (with translation).

* cited by examiner

*Primary Examiner* — Aarti B Berdichevsky
(74) *Attorney, Agent, or Firm* — Oliff PLC (57) ABSTRACT

A balloon catheter includes a core wire and an opening control portion. The core wire is formed of a long wire disposed in an outer shaft and includes a pushing portion. The opening control portion is provided in the outer shaft and has a control hole that communicates with an inflation lumen. The opening area of the control hole in the opening control portion is partially closed when the pushing portion of the core wire comes into contact with the control hole.

9 Claims, 4 Drawing Sheets

BALLOON CATHETER

CROSS-REFERENCE TO RELATED APPLICATION

This application claims priority to Japanese Patent Application No. 2011-047083 filed in the Japan Patent Office on Mar. 4, 2011, the entire contents of which are incorporated by reference herein.

BACKGROUND

The disclosed embodiments relate to balloon catheters used to dialate a stenosis or the like in a body cavity, such as a blood vessel. Balloon catheters have generally been used to dilate a stenosis or the like in a body cavity, such as a blood vessel. An example of a balloon catheter mainly includes a balloon, which is an inflatable body, an outer shaft, and an inner shaft disposed inside the outer shaft. The inner shaft allows a guidewire to be inserted therethrough. The outer shaft forms an inflation lumen between the inner shaft and an inner surface of the outer shaft. Liquid, such as a contrast medium or physiological saline solution, for inflating the balloon is caused to flow through the inflation lumen.

To move the balloon catheter to a desired position in a blood vessel or the like, an operator, such as a doctor, applies a pushing force to the catheter at a proximal portion thereof to insert the catheter into the body by pushing the catheter in an axial direction. The balloon catheter is required to have a high pushing-force transmission performance, which is the performance of transmitting the pushing force from the proximal portion to a distal portion thereof.

There are some balloon catheters in which a core wire is disposed in an outer shaft to increase the pushing-force transmission performance and adjust rigidity variation in the balloon catheters (see, for example, Japanese Unexamined Patent Application Publication No. 2002-291899 and Japanese Unexamined Patent Application Publication (Translation of PCT Application) No. 2002-505166). In such a balloon catheter that includes a core wire, a distal end portion of the core wire may be fixed to a part of the catheter to further increase the pushing-force transmission performance (see, for example, Japanese Unexamined Patent Application Publication (Translation of PCT Application) Nos. 2003-517901, 8-500505, and 9-503411).

SUMMARY

Although the above-described balloon catheters according to the related art may achieve increased pushing-force transmission performance, there has been a demand to further increase the pushing-force transmission performance. However, if the thickness of the core wire is increased to improve the pushing-force transmission performance, the cross sectional area of the inflation lumen in which the core wire is arranged will be reduced accordingly. Therefore, a so-called deflate time, which is the time necessary to discharge the liquid with which the balloon has been inflated through the inflation lumen to deflate the balloon, will be increased.

The disclosed embodiments have been made in view of the above-described situation. An object of the invention is to provide a balloon catheter capable of reliably transmitting a pushing force applied at a proximal portion of the balloon catheter to a distal portion of the balloon catheter and quickly discharging the liquid used to inflate the balloon from the balloon.

The above-described object is achieved by the following means.

A balloon catheter according to an aspect of the present invention includes a balloon, a cylindrical outer shaft, an opening control portion, and a core wire. At least a part of the balloon is attached to the outer shaft. The outer shaft forms an inflation lumen through which fluid for inflating the balloon is supplied. The opening control portion is provided on the outer shaft, and has a control hole that communicates with the inflation lumen. The core wire is formed of a long wire disposed in the outer shaft. The core wire includes a pushing portion that is capable of coming into contact with the control hole in the opening control portion.

DETAILED DESCRIPTION OF EMBODIMENTS

A balloon catheter according to an embodiment of the present invention includes a balloon, a cylindrical outer shaft, an opening control portion, and a core wire. At least a part of the balloon is attached to the outer shaft. The outer shaft forms an inflation lumen through which fluid for inflating the balloon is supplied. The opening control portion is provided on the outer shaft, and has a control hole that communicates with the inflation lumen. The core wire is formed of a long wire disposed in the outer shaft. The core wire includes a pushing portion that is capable of coming into contact with the control hole in the opening control portion.

The balloon catheter may further include an inner shaft that is disposed in the outer shaft and in which a guidewire lumen for allowing a guidewire to be inserted therethrough is formed, a front guidewire port formed at a distal end of the inner shaft, and a rear guidewire port formed at a proximal end of the inner shaft, the rear guidewire port being formed in the opening control portion.

In the balloon catheter, the control hole in the opening control portion may include a first hole section and a second hole section, the first hole section having an opening that is closed when the pushing portion comes into contact with the first hole section and the second hole section having an opening that is constantly open.

The balloon catheter according to the embodiment of the present invention gradually transmits the pushing force applied by an operator, such as a doctor, from the proximal portion to the distal portion of the outer shaft. In addition, in the balloon catheter according to the embodiment of the present invention, the pushing portion of the core wire blocks the control hole and pushes the opening control portion so as to transmit the pushing force. Thus, the pushing-force transmission performance can be increased.

When the inflation fluid is discharged from the balloon, the pushing portion of the core wire is removed from the control hole to open the entire area of the control hole. Therefore, the inflation fluid can be discharged through the entire area of the control hole, and the balloon can be quickly deflated. Even when the pushing force is applied to the core wire and the control hole is partially closed, the inflation fluid can be discharged since the remaining part of the control hole is constantly open.

In the case where the rear guidewire port is formed in the opening control portion, the proximal end of the inner shaft is pushed by the pushing portion of the core wire. Therefore, the pushing force can also be transmitted to the inner shaft. Thus, the pushing force applied at the proximal portion of the catheter can be effectively transmitted to the distal portion of the balloon catheter. In other words, the pushing-force transmission performance of the balloon catheter can be increased.

In the case where the control hole in the opening control portion includes the first hole section having an opening that is closed when the pushing portion comes into contact therewith and the second hole section that is constantly open, the pushing portion can be brought into contact with substantially the entire periphery of the control hole. Therefore, the contact area between the pushing portion and the opening control portion is increased and the pushing force can be effectively transmitted.

In addition, the opening area that is constantly open is provided by the second hole section. Therefore, the balloon can be effectively deflated.

Figure 1:
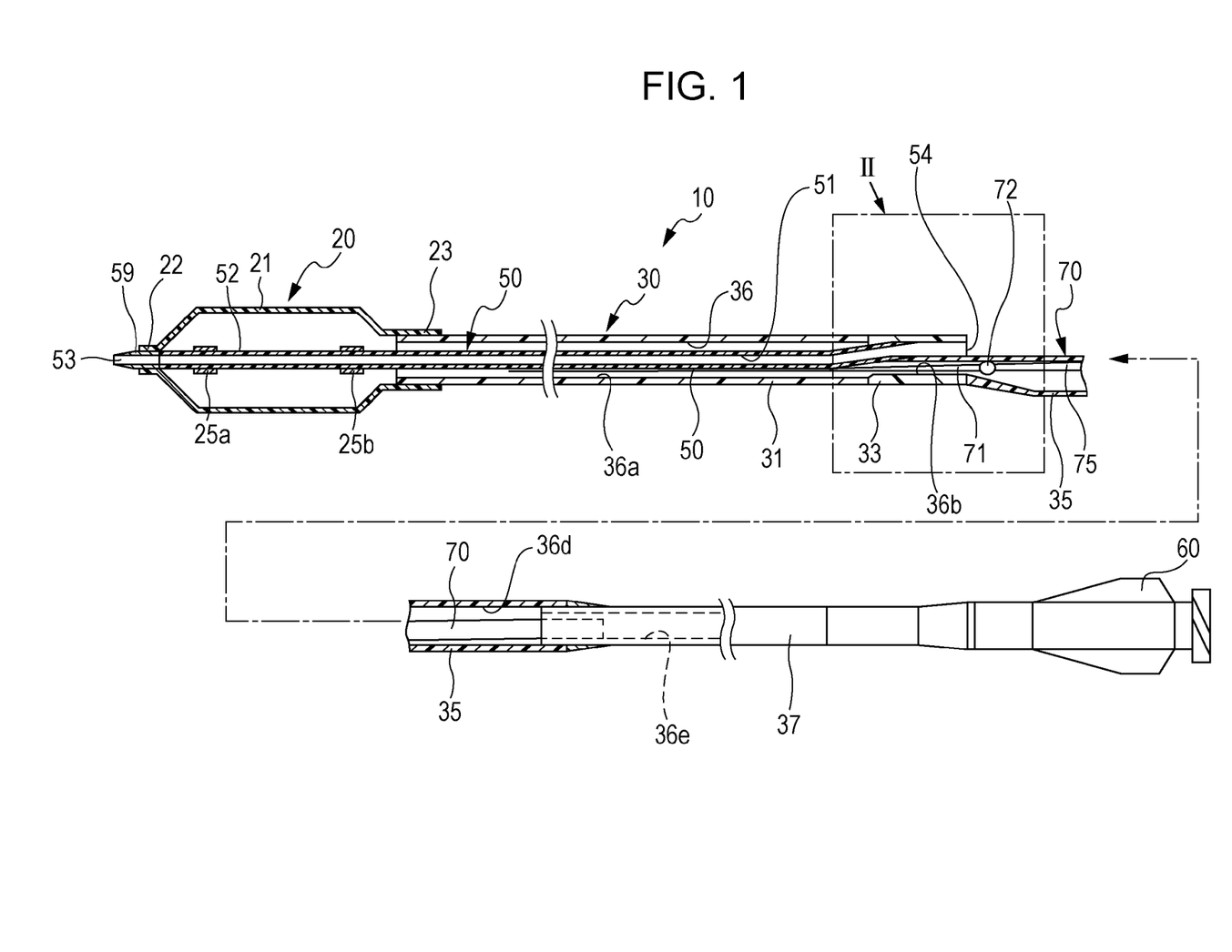
FIG. 1 illustrates the entire body of a balloon catheter according to an embodiment.
Figure 2:
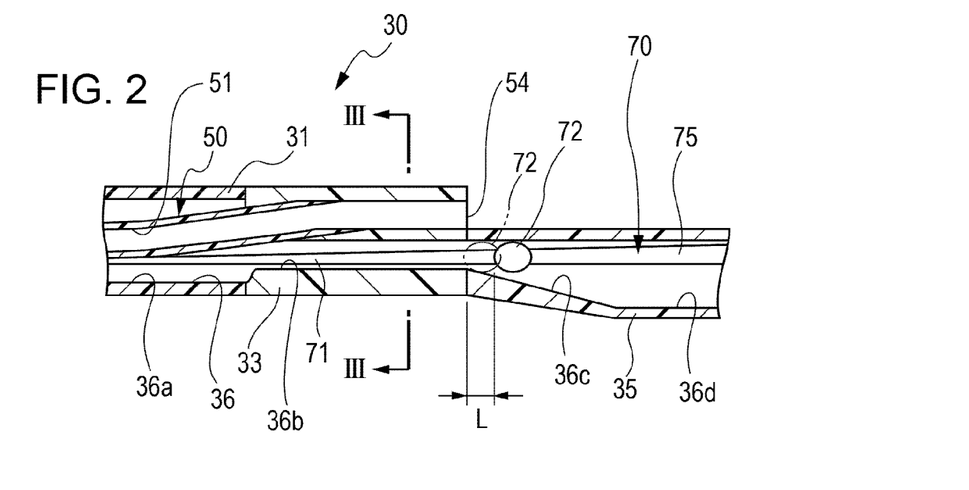
FIG. 2 is an enlarged view of part II in FIG. 1.

A balloon catheter 10 according to an embodiment will be described with reference to FIGS. 1 to 3. In FIGS. 1 and 2, the left side corresponds to the distal end (front end) from which the balloon catheter 10 is inserted into the body and the right side corresponds to the proximal end (rear end, base end) at which the balloon catheter 10 is operated by an operator, such as a doctor.

The balloon catheter 10 is used to treat, for example, an occlusion or a stenosis of a blood vessel of a heart. The overall length of the balloon catheter 10 is about 1,500 mm. The balloon catheter 10 mainly includes a balloon 20, an outer shaft 30, an inner shaft 50, and a connector 60.

The balloon 20 is made of resin and includes an inflatable portion 21 at a central area in an axial direction of the balloon 20, a front attachment portion 22 at the front end of the balloon 20, and a rear attachment portion 23 at the rear end of the balloon 20. The inflatable portion 21 is a portion of the balloon 20 that inflates.

The front attachment portion 22 is fixed to a front end portion of an extending portion 52 of the inner shaft 50, which will be described below. The rear attachment portion 23 is fixed to an outer surface of the outer shaft 30 at a distal end thereof.

The outer shaft 30 is a cylindrical member that forms an inflation lumen 36 for supplying the fluid for inflating the balloon 20. The outer shaft 30 includes a front outer shaft portion 31, an opening control portion 33, an intermediate outer shaft portion 35, and a rear outer shaft portion 37 in that order from the distal end thereof. The front outer shaft portion 31 and the intermediate outer shaft portion 35 are resin tubes. The opening control portion 33 is formed by bonding the front outer shaft portion 31, the intermediate outer shaft portion 35, and the inner shaft 50 together by welding. The resin used to form the front outer shaft portion 31 and the intermediate outer shaft portion 35 may be, for example, a polyamide, a polyamide elastomer, a polyolefin, a polyester, or a polyester elastomer.

The rear attachment portion 23 of the balloon 20 is fixed to the outer surface of the front outer shaft portion 31 at the distal end thereof. The inner shaft 50 is disposed in the front outer shaft portion 31. A front inflation lumen 36a, which forms as a front portion of the inflation lumen 36, is formed between the front outer shaft portion 31 and the inner shaft 50.

The outer diameter of the front outer shaft portion 31 is substantially equal to the outer diameter of the opening control portion 33. The outer diameter of the front outer shaft portion 31 may be set from about 0.85 mm to about 0.95 mm, and is set to about 0.90 mm in the present embodiment. The inner diameter of the front outer shaft portion 31 may be set from about 0.69 mm to about 0.80 mm, and is set to about 0.75 mm in the present embodiment.

In the opening control portion 33, the front outer shaft portion 31 and the intermediate outer shaft portion 35 are bonded together and the rear end of the inner shaft 50 is attached to the outer shaft 30 to form a rear guidewire port 54. These members are bonded together by welding. Therefore, the material of the opening control portion 33 includes a fused mixture of resins that form the above-mentioned members.

The length of the opening control portion 33 in the axial direction may be set from about 3.0 mm to about 7.0 mm, and is set to about 5.0 mm in the present embodiment.

The opening control portion 33 has a control hole 36b. As illustrated in FIG. 3, the control hole 36b includes a first hole section 36b1 and a second hole section 36b2 that are arranged next to each other in a direction orthogonal to the axial direction of the outer shaft 30. The first hole section 36b1 allows a core wire 70, which will be described below, to extend therethrough. The first hole section 36b1 is closed when a pushing portion 72 of the core wire 70 comes into contact therewith. When the pushing portion 72 of the core wire 70 is not in contact with the first hole section 36b1, the opening of the first hole section 36b1 at the front end thereof communicates with the front inflation lumen 36a and the opening of the first hole section 36b1 at the rear end thereof communicates with an intermediate inflation lumen 36d through a guiding portion 36c.

The core wire 70 is not inserted through the second hole section 36b2, and the second hole section 36b2 is constantly open. Therefore, the opening of the second hole section 36b2 at the front end thereof constantly communicates with the front inflation lumen 36a, and the opening of the second hole section 36b2 at the rear end thereof constantly communicates with the intermediate inflation lumen 36d through the guiding portion 36c.

The first hole section 36b1 and the second hole section 36b2 have substantially circular cross sections that slightly overlap so that the first hole section 36b1 and the second hole section 36b2 communicate with each other and form a single hollow space. The first hole section 36b1 and the second hole section 36b2 are formed simultaneously when the front outer shaft portion 31, the intermediate outer shaft portion 35, and the inner shaft 50 are welded together. More specifically, the front outer shaft portion 31, the intermediate outer shaft portion 35, and the inner shaft 50 are welded together while two mandrels for forming the first hole section 36b1 and the second hole section 36b2 are inserted through the front outer shaft portion 31 and the intermediate outer shaft portion 35. Then, the two mandrels are extracted. Thus, the first hole section 36b1 and the second hole section 36b2 can be easily formed.

The opening area of the first hole section 36b1 and that of the second hole section 36b2 are equal to each other. The diameter D of the first hole section 36b1 and the second hole section 36b2 may be set from about 0.20 mm to about 0.30 mm, and is set to about 0.25 mm in the present embodiment.

The first hole section 36b1 and the second hole section 36b2 partially overlap each other, and have circular shapes that are partially cut at sections in which they overlap. However, the first hole section 36b1 and the second hole section 36b2 have independent circular outer shapes.

The intermediate outer shaft portion 35 is a cylindrical resin tube. The intermediate outer shaft portion 35 includes the guiding portion 36c and the intermediate inflation lumen 36d. The guiding portion 36c communicates with the control hole 36b in the opening control portion 33 and forms a part of the inflation lumen 36.

The guiding portion 36c is a tapered passage and is connected to the control hole 36b. The pushing portion 72 of the core wire 70, which will be described below, is guided toward the front end of the outer shaft 30 by the guiding portion 36c so that the opening of the first hole section 36b1 at the rear end thereof is closed and pushed by the pushing portion 72. At this time, the pushing portion 72 pushes the substantially circular rim of the first hole section 36b1, so that the pushing force applied to the core wire 70 can be transmitted to the outer shaft 30 through the opening control portion 33.

The intermediate inflation lumen 36d is a passage having a constant outer diameter, and forms a lumen in the intermediate outer shaft portion 35 in an area other than the guiding portion 36c.

The length of the intermediate outer shaft portion 35 in the axial direction may be set in the range of about 150.0 mm to about 200.0 mm, and is set to about 160.0 mm in the present embodiment. The outer diameter of a part of the intermediate outer shaft portion 35 that has a constant outer diameter and in which the intermediate inflation lumen 36d is formed may be set from about 0.80 mm to about 0.90 mm, and is set to about 0.85 mm in the present embodiment. The inner diameter of this part of the intermediate outer shaft portion 35 may be set from about 0.65 mm to about 0.80 mm, and is set to about 0.75 mm in the present embodiment.

The rear outer shaft portion 37 is a tubular member made of metal that is generally called a hypotube. A front end portion of the rear outer shaft portion 37 is inserted into and fixed to a rear end portion of the intermediate outer shaft portion 35. A rear inflation lumen 36e is formed in the rear outer shaft portion 37. The above-described front inflation lumen 36a, the control hole 36b, the guiding portion 36c, the intermediate inflation lumen 36d, and the rear inflation lumen 36e form the inflation lumen 36.

A connector 60 is attached to the rear outer shaft portion 37 at the rear end thereof. Liquid, such as a contrast medium or physiological saline solution, for inflating the balloon 20 is supplied from an indeflator (not shown) attached to the connector 60. The supplied liquid flows through the inflation lumen 36 and inflates the balloon 20.

The outer diameter of the rear outer shaft portion 37 may be in the range of about 0.60 mm to about 0.65 mm, and is set to about 0.64 mm in the present embodiment. The inner diameter of the rear outer shaft portion 37 may be in the range of about 0.40 mm to about 0.50 mm, and is set to about 0.48 mm in the present embodiment. The material of the rear outer shaft portion 37 is not particularly limited, and stainless steel is used in the present embodiment. Alternatively, a superelastic alloy, such as Ni—Ti alloy, may be used.

Figure 3:
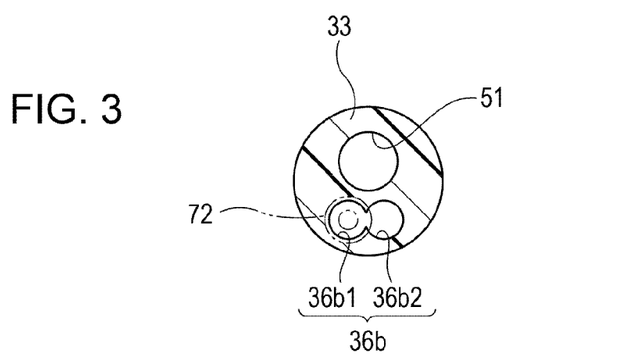
FIG. 3 is a sectional view of FIG. 2 taken along line III-III.

In FIGS. 1 to 3, the dimensions of the front outer shaft portion 31, the opening control portion 33, the intermediate outer shaft portion 35, and the rear outer shaft portion 37 are exaggerated to clarify the structures thereof.

The core wire 70 is attached to the inner surface of the rear outer shaft portion 37 at the distal end thereof. The core wire 70 has a circular cross section, and is formed of a metal wire that is tapered such that the diameter thereof decreases toward the distal end of the core wire 70. In the present embodiment, the diameter of the core wire 70 gradually decreases from about 0.40 mm to about 0.10 mm toward the distal end of the core wire 70. The material of the core wire 70 is not particularly limited, and stainless steel (SUS304) is used in the present embodiment. Alternatively, a superelastic alloy, such as Ni—Ti alloy, or a piano wire may be used.

The core wire 70 extends through the intermediate outer shaft portion 35 and the first hole section 36b1 in the opening control portion 33 to a distal portion of the front outer shaft portion 31. The pushing portion 72 is attached to the core wire 70 at a position closer to the proximal end of the first hole section 36b1 in the opening control portion 33. Thus, the core wire 70 can be divided into a front core portion 71 that is on the front side of the pushing portion 72 and a main core portion 75 that is on the rear side of the pushing portion 72.

The rear end of the main core portion 75 is fixed to the inner wall of the rear outer shaft portion 37 at the distal end thereof by soldering or laser welding.

As described above, the pushing portion 72 is positioned closer to the proximal end of the first hole section 36b1 in the opening control portion 33. When a pushing force is applied to the core wire 70, the pushing portion 72 is moved toward the front end of the outer shaft 30 to the position shown by the two-dot chain line in FIG. 2. Accordingly, the pushing portion 72 is fitted to the opening of the first hole section 36b1 and closes the opening of the first hole section 36b1. The shape and size of the pushing portion 72 are not particularly limited as long as the opening of the first hole section 36b1 can be closed by the pushing portion 72 as described above. In the present embodiment, the pushing portion 72 has an ellipsoidal shape. In addition, the maximum diameter of the pushing portion 72 in a direction orthogonal to the axial direction of the core wire 70 is set to be larger than the diameter of the first hole section 36b1.

When the pushing force is applied to the core wire 70, the pushing portion 72 closes the opening of the first hole section 36b1. When no pushing force is applied to the core wire 70, the pushing portion 72 opens the opening of the first hole section 36b1 and allows the liquid for inflating the balloon 20 to flow through the first hole section 36b1. In a normal state in which no pushing force is applied to the core wire 70, the pushing portion 72 is not in contact with the opening of the first hole section 36b1 but is spaced therefrom by a small distance L. When the pushing force is applied to the balloon catheter 10, the intermediate outer shaft portion 35 or the other outer shaft portion contracts. Accordingly, the pushing portion 72 comes into contact with the opening of the first hole section 36b1. The distance L varies in accordance with, for example, an amount by which the intermediate outer shaft portion 35 is bent when the pushing force is applied thereto. The distance L may be set from about 0.5 mm to about 2.0 mm, and is set to about 1.0 mm in the present embodiment.

The pushing force is a force applied by an operator, such as a doctor, to push the balloon catheter 10 forward in the axial direction and advance the balloon catheter in the body.

The front core portion 71 extends through the first hole section 36b1 in the opening control portion 33 to the distal portion of the front outer shaft portion 31. The front core portion 71 gives rigidity variation to the balloon catheter 10 in the axial direction thereof. In addition, since the front core portion 71 extends through the first hole section 36b1, when the pushing force is applied, the pushing portion 72 reliably moves toward the front end of the outer shaft 30 along the guiding portion 36c, comes into contact with the opening of the first hole section 36b1, and blocks the opening.

The length of the front core portion 71 in the axial direction is set in the range of about 5.0 mm to about 150.0 mm, and is set to about 130.0 mm in the present embodiment.

With the above-described structure, when the pushing force, which is the force in the axial direction from the rear end of the outer shaft 30 toward the front end thereof, is applied to the core wire 70, the front end of the pushing portion 72 blocks and pushes the first hole section 36b1 in the opening control portion 33. Accordingly, the outer shaft 30 is pushed toward the front end thereof. In the normal state in which no pushing force is applied to the core wire 70, the pushing portion 72 is separated from the opening of the first hole section 36b1. Accordingly, the entire area of the control hole 36b including the first hole section 36b1 and the second hole section 36b2 is opened to allow the liquid for inflating the balloon 20 to flow therethrough.

The inner shaft 50 is substantially coaxially disposed in the front outer shaft portion 31. The inner shaft 50 is a cylindrical member made of a resin similar to those used to form the front outer shaft portion 31 and the intermediate outer shaft portion 35. The inner shaft 50 has a guidewire lumen 51 which allows a guidewire to be inserted therethrough. The front inflation lumen 36a, which forms the front portion of the inflation lumen 36, is formed between the inner surface of the front outer shaft portion 31 and the outer surface of the inner shaft 50. The proximal end of the inner shaft 50 is welded to the opening control portion 33 of the outer shaft 30 in a manner such that the rear guidewire port 54 is formed.

The inner shaft 50 includes the extending portion 52 at the front end portion thereof. The extending portion 52 projects from the front end of the front outer shaft portion 31, and a tip 59 is attached to the extending portion 52 at the front end thereof. The tip 59 has a tapered outer shape such that the outer diameter thereof gradually decreases toward the front end, and is formed of a soft resin. The tip 59 is a tubular member that forms a front end portion of the guidewire lumen 51, and has a front guidewire port 53 at the front end thereof.

The front attachment portion 22 of the balloon 20 is fixed to the distal end of the extending portion 52 of the inner shaft 50.

A pair of radiopaque markers 25a and 25b that are spaced from each other by a predetermined distance are attached to the extending portion 52 of the inner shaft 50 in the inflatable portion 21 of the balloon 20.

An operation of dilating a stenosis of a coronary artery of a heart by using the balloon catheter 10 according to the present embodiment having the above-described structure will now be described.

A guidewire (not shown) is beforehand inserted into the coronary artery of the heart having the stenosis, which is the treatment target. The balloon catheter 10 is inserted into the body along the guidewire. The guidewire is inserted into the front guidewire port 53 in the tip 59 of the balloon catheter 10, and is caused to pass through the guidewire lumen 51 in the inner shaft 50 and exit from the rear guidewire port 54.

To advance the balloon catheter 10 along the guidewire in the blood vessel, the operator, such as a doctor, pushes the balloon catheter 10 in the axial direction at the proximal portion thereof. The pushing force applied in this process is transmitted from the rear outer shaft portion 37, which is a metal tube, toward the distal end of the balloon catheter 10 through the intermediate outer shaft portion 35, the opening control portion 33, and the front outer shaft portion 31, which are made of resin, in that order.

The pushing force is also transmitted from the rear outer shaft portion 37 to the core wire 70 that is attached to the rear outer shaft portion 37. At the same time, the intermediate outer shaft portion 35 or the other outer shaft portion is bent so that the pushing portion 72 of the core wire 70 is moved along the guiding portion 36c and block the first hole section 36b1 of the control hole 36b. Accordingly, the pushing portion 72 pushes the proximal end of the opening control portion 33. In other words, the core wire 70 directly pushes the outer shaft 30 at the opening control portion 33. Therefore, the pushing force can be effectively transmitted toward the distal end of the outer shaft 30.

The core wire 70 pushes the rear end of the opening control portion 33, to which the proximal end of the inner shaft 50 is attached. Therefore, the pushing force applied at the proximal end is also transmitted to the inner shaft 50. Therefore, the pushing force can be transmitted toward the distal end of the balloon catheter 10 not only by the outer shaft 30 but also by the inner shaft 50. Therefore, the pushing force can be effectively transmitted to the tip 59 at the front end of the balloon catheter 10.

The operator advances the balloon 20 to the stenosis, which is the target, by using the markers 25a and 25b under radioscopic observation. Then, inflation liquid, such as a contrast medium or physiological saline solution, used to inflate the balloon 20 is supplied from the indeflator (not shown) that is connected to the connector 60. The inflation liquid flows into the inflation lumen 36 in the outer shaft 30. Even when the pushing force is applied to the core wire 70 and the first hole section 36b1 of the control hole 36b is blocked, the second hole section 36b2 is constantly open. Therefore, the inflation liquid passes through the opening control portion 33 at least along the second hole section 36b2 of the control hole 36b and flows out of the front outer shaft portion 31 at the front end thereof to inflate the balloon 20.

When the operation of dilating the stenosis with the balloon 20 is finished, the operator discharges the inflation liquid from the balloon 20 by using the indeflator. Since the balloon 20 is already positioned when the balloon 20 is deflated, the pushing force is probably not applied to the core wire 70 at this time. In such a case, the pushing portion 72 of the core wire 70 is separated from the first hole section 36b1 and the entire area of the control hole 36b is open. Accordingly, the inflation liquid is discharged to the rear inflation lumen 36e in the rear outer shaft portion 37 through both of the first hole section 36b1 and the second hole section 36b2, so that the balloon 20 can be quickly deflated.

Even if the pushing force is applied to the core wire 70 and the first hole section 36b1 is blocked, the second hole section 36b2 is constantly open. Therefore, the inflation liquid can be discharged to the rear inflation lumen 36e in the rear outer shaft portion 37 through the second hole section 36b2 of the control hole 36b, so that the balloon 20 can be deflated. Then, the balloon catheter 10 is extracted from the body, and the operation is thus completed.

As described above, according to the balloon catheter 10 of the present embodiment, the pushing force applied by the operator is not only transmitted from the proximal portion of the outer shaft 30 toward the distal portion thereof, but is also transmitted at an intermediate position of the outer shaft 30 by causing the pushing portion 72 of the core wire 70 to push the opening control portion 33.

In addition, since the proximal end of the inner shaft 50 is bonded to the opening control portion 33, the pushing portion 72 pushes the proximal end of the inner shaft 50. Therefore, the pushing force can also be transmitted to the inner shaft 50. Accordingly, the pushing force applied at the proximal end of the balloon catheter 10 can be effectively transmitted to the tip 59 at the front end of the balloon catheter 10. In other words, the pushing-force transmission performance of the balloon catheter 10 can be increased.

When the inflation liquid is discharged from the balloon 20, the pushing portion 72 of the core wire 70 is separated from the first hole section 36b1 and the entire area of the control hole 36b is open. Therefore, the inflation liquid can be discharged to the rear inflation lumen 36e in the rear outer shaft portion 37 through both of the first hole section 36b1 and the second hole section 36b2, and the balloon 20 can be quickly deflated. Even if the pushing force is applied to the core wire 70 and the first hole section 36b1 is blocked, the second hole section 36b2 is constantly open. Therefore, the inflation liquid can be discharged through the second hole section 36b2 of the control hole 36b, so that the balloon 20 can be deflated.

Figure 4:
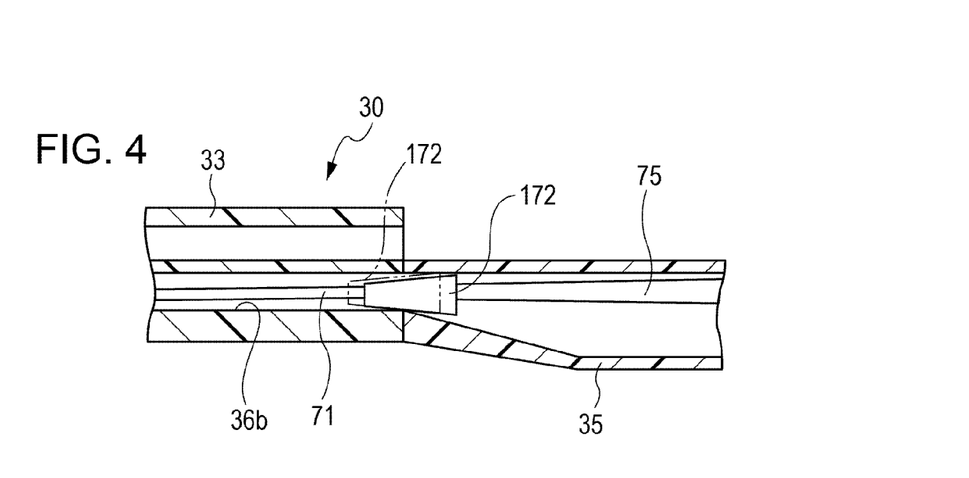
FIG. 4 illustrates a pushing portion according to another embodiment.

In the above-described embodiment, the pushing portion 72 has an ellipsoidal shape. However, the pushing portion 72 may instead have various other shapes such as a spherical shape and a conical shape whose diameter decreases toward the distal end thereof. For example, as illustrated in FIG. 4, a pushing portion 172 having a conical shape whose diameter decreases toward the distal end thereof may be provided. In a normal state in which no pushing force is applied, a distal end portion of the pushing portion 172 is inserted in the first hole section 36b1 in a manner such that a gap is provided between the distal end portion and the first hole section 36b1. Thus, the first hole section 36b1 is in an open state. When the pushing force is applied, the pushing portion 172 is moved toward the front end of the outer shaft 30 to the position shown by the two-dot chain line. Accordingly, the pushing portion 172 blocks the opening of the first hole section 36b1 and pushes the rear end of the opening control portion 33.

According to the above-described embodiment, the pushing portion 72 is separated from the opening of the first hole section 36b1 by the distance L in the normal state in which no pushing force is applied. However, the pushing portion 72 may substantially be in contact with the opening of the first hole section 36b1 in the normal state. In this case, when the inflation liquid is discharged from the balloon 20, an axial stretching force caused by the discharged liquid is applied to the outer shaft 30 including the intermediate outer shaft portion 35 to separate the pushing portion 72 from the opening of the first hole section 36b1 so the inflation liquid can be discharged through the first hole section 36b1.

Figure 5:
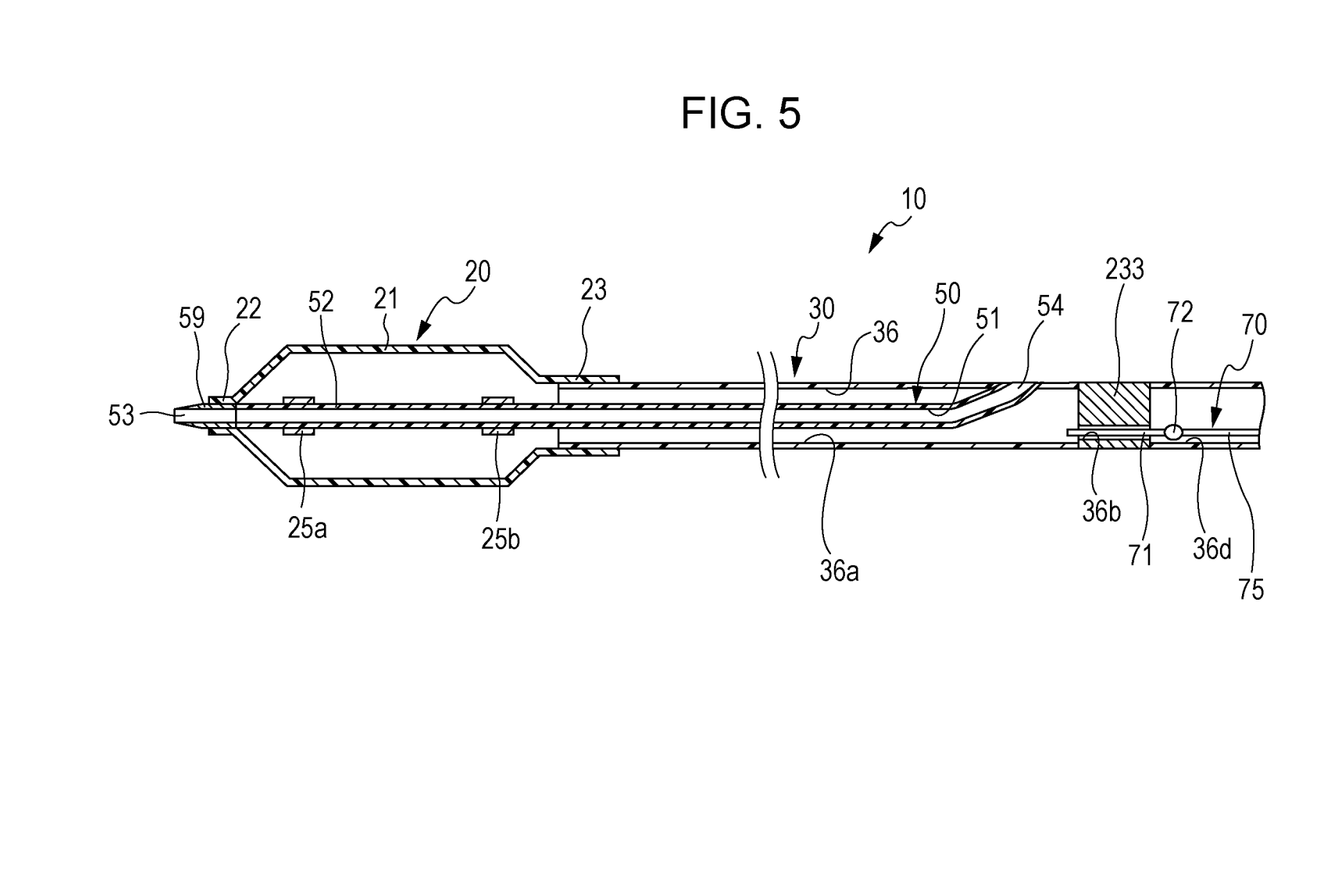
FIG. 5 illustrates an opening control portion according to another embodiment.

In the above-described embodiment, the proximal end of the inner shaft 50 is bonded to the opening control portion 33 having the control hole 36b. However, as illustrated in FIG. 5, an opening control portion 233 may be separated from the proximal end of the inner shaft 50. The opening control portion 233 illustrated in FIG. 5 is at a position separated from the rear guidewire port 54 toward the rear end by a predetermined distance.

In the embodiment illustrated in FIG. 5, the above-described guiding portion 36c is omitted. When the guiding portion 36c is formed, the pushing portion 72 can be reliably guided to the opening of the first hole section 36b1 to close the opening. However, the effect of guiding the pushing portion 72 to the opening of the first hole section 36b1 can be achieved as long as the front core portion 71 is inserted through the first hole section 36b1. Therefore, the guiding portion 36c may be omitted. It is not necessary that the front core portion 71 have a long length in the axial direction as in the above-described embodiment as long as the pushing portion 72 can be guided to the opening of the first hole section 36b1. As illustrated in FIG. 5, the length of the front core portion 71 in the axial direction may be as short as the length substantially equal to that of the opening control portion 233 in the axial direction.

The opening control portion may be disposed at a position separated from the rear guidewire port 54 in a direction opposite to that in the embodiment illustrated in FIG. 5, that is, toward the front end by a predetermined distance.

Figure 6A:
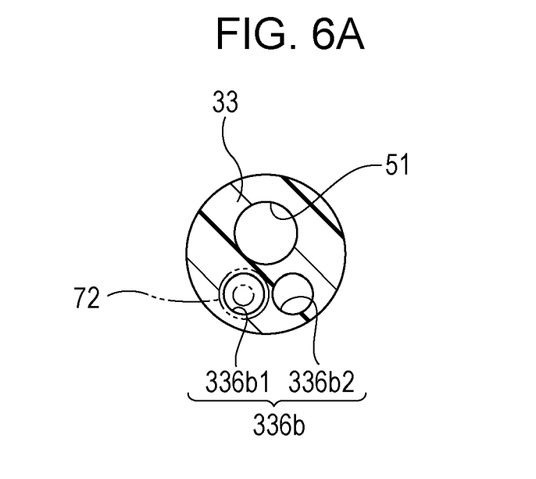
FIGS. 6A and 6B illustrate control holes according to other embodiments.

In the above-described embodiment, the control hole 36b includes the first hole section 36b1 and the second hole section 36b2 that overlap. However, the shape and structure of the control hole 36b are not limited to this, and the control hole 36b may have various other shapes and structures. For example, as illustrated in FIG. 6A, a control hole 336b may be formed so as to include a first hole section 336b1 and a second hole section 336b2 that are completely separated from each other.

Figure 6B:
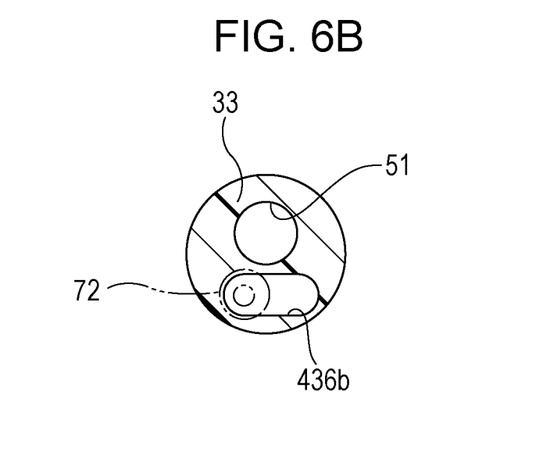

Alternatively, as illustrated in FIG. 6B, a single hole 436b having an elliptical shape may be formed instead of the control hole 36b. In this case, the pushing portion 72 of the core wire 70 blocks about a half of the opening of the hole 436b as shown by the two-dot chain line. In the embodiments illustrated in FIGS. 4 to 6, parts similar to those illustrated in FIGS. 1 to 3 are denoted by the same reference numerals.

According to the above-described embodiment, the balloon catheter 10 is used in the treatment of a blood vessel of a heart. However, the balloon catheter 10 may be used in various other operations, such as an operation of dilating a blood vessel in a lower limb or a shunt for dialysis.

What is claimed is:

1. A balloon catheter comprising:
    a balloon;
    a cylindrical outer shaft to which at least a part of the balloon is attached, the cylindrical outer shaft forming an inflation lumen through which fluid for inflating the balloon is supplied;
    an opening control portion provided in the cylindrical outer shaft and having a control hole that communicates with the inflation lumen;
    a core wire formed of an elongated wire disposed in the cylindrical outer shaft, the core wire: i) being slideable along a longitudinal direction of the balloon catheter, and ii) including a pushing portion that is selectively engageable and disengageable with the control hole in the opening control portion;
    an inner shaft that is disposed in the cylindrical outer shaft and in which a guidewire lumen for allowing a guidewire to be inserted therethrough is formed;
    a front guidewire port formed at a distal end of the inner shaft; and
    a rear guidewire port formed at a proximal end of the inner shaft, wherein
    the rear guidewire port is formed in the opening control portion.

2. The balloon catheter according to claim 1, wherein the core wire has a diameter that gradually decreases from about 0.40 mm to about 0.10 mm toward a distal end of the core wire.

3. The balloon catheter according to claim 1, wherein the inner shaft includes a pair of radiopaque markers that are spaced from each other by a predetermined distance.

4. The balloon catheter according to claim 1, wherein the pushing portion does not contact the control hole when no pushing force is applied to the core wire.

5. The balloon catheter according to claim 1, wherein the pushing portion is tapered.

6. The balloon catheter according to claim 5, wherein the pushing portion has a non-uniform width.

7. The balloon catheter according to claim 1, wherein the control hole in the opening control portion includes a first hole section and a second hole section, the first hole section having an opening that is closed when the pushing portion engages with the first hole section and the second hole section having an opening that is constantly open.

8. The balloon catheter according to claim 7, wherein the first hole section and the second hole section partially overlap each other, and have circular shapes that are partially cut at sections in which the first hole section and the second hole section overlap.

9. A balloon catheter comprising:
   a balloon;
   a cylindrical outer shaft to which at least a part of the balloon is attached, the cylindrical outer shaft forming an inflation lumen through which fluid for inflating the balloon is supplied;
   an opening control portion provided in the cylindrical outer shaft and having a control hole that communicates with the inflation lumen;
   a core wire formed of an elongated wire disposed in the cylindrical outer shaft, the core wire: i) being slideable along a longitudinal direction of the balloon catheter, and ii) including a pushing portion that is selectively engageable and disengageable with the control hole in the opening control portion;
   an inner shaft that is disposed in the cylindrical outer shaft and in which a guidewire lumen for allowing a guidewire to be inserted therethrough is formed;
   a front guidewireport formed at a distal end of the inner shaft; and
   a rear guidewire port formed at a proximal end of the inner shaft, wherein
   the rear guidewire port is formed in the opening control portion, and
   a maximum diameter of the pushing portion is larger than a maximum diameter of the control hole.

* * * * *